United States Patent [19]
Gohno et al.

[11] Patent Number: 5,590,165
[45] Date of Patent: Dec. 31, 1996

[54] METHOD FOR GENERATING FAT DISTRIBUTION IMAGE BY CT SYSTEM

[75] Inventors: Makoto Gohno; Tetsuya Horiuchi, both of Tokyo, Japan

[73] Assignee: GE Yokogawa Medical Systems, Limited, Tokyo, Japan

[21] Appl. No.: 335,772

[22] PCT Filed: May 25, 1993

[86] PCT No.: PCT/JP93/00696
§ 371 Date: Nov. 9, 1994
§ 102(e) Date: Nov. 9, 1994

[87] PCT Pub. No.: WO93/24054
PCT Pub. Date: Dec. 9, 1993

[30] Foreign Application Priority Data

May 26, 1992 [JP] Japan .................................. 4-133204

[51] Int. Cl.$^6$ .................................................. A61B 6/03
[52] U.S. Cl. .................. 378/18; 378/5; 378/901; 364/413.15
[58] Field of Search ............... 364/413.15, 413.16; 378/5, 18, 901

[56] References Cited

U.S. PATENT DOCUMENTS

| | | | |
|---|---|---|---|
| 4,922,915 | 5/1990 | Arnold et al. | 128/653 R |
| 4,985,906 | 1/1991 | Arnold | 378/18 |
| 5,222,021 | 6/1993 | Feldman et al. | 364/413.14 |

Primary Examiner—David P. Porta
Assistant Examiner—David Vernon Bruce
Attorney, Agent, or Firm—Moonray Kojima

[57] ABSTRACT

A method of generating an image representing fat distributions, comprising the steps of scanning two different levels of tube voltage using a phantom containing a sample rod of a fat standard material and a plurality of sample rods with different densities of a bone mineral equivalent material, to generate two cross sectional image data; detecting the CT number of each pixel in an entire region or an objective region of the cross sectional image data as the CT number of a tissue including fat ($\alpha wf$); detecting the CT number of the bone mineral equivalent material to calculate a linear regression between the CT number and the density of the bone mineral equivalent material and to define the CT number of a tissue excluding fat ($\alpha nf$); detecting the CT number of the fat standard material ($\alpha ff$), while detecting the CT number of a soft tissue standard material ($\alpha st$), wherein individual CT numbers are applied to the equation $$\alpha wf = \alpha nf + \beta \cdot (\alpha ff - \alpha st)$$

with $\beta$ defined as a fat ratio parameter; calculating the fat ratio parameter $\beta$ of each pixel in the entire region or an objective region of the cross sectional image data using the foregoing equation, with attention focused on the finding that the density of the bone mineral equivalent material is constant at scanning at any different level of tube voltage, and finally generating an image based on the fat ratio parameter $\beta$.

2 Claims, 3 Drawing Sheets

METHOD FOR GENERATING FAT DISTRIBUTION IMAGE BY CT SYSTEM

TECHNICAL FIELD

The present invention relates to a method for generating a fat distribution image by a CT system. More particularly, the present invention relates to a method for generating a fat distribution image by a CT system, wherein an image of fat distribution is generated from a cross sectional image data via X ray.

BACKGROUND ART

As the method for generating a fat distribution image from a cross sectional image data via X ray, a method is known comprising determining a threshold value so as to extract the CT number range from −130 to −100 from the cross sectional image data, based on the finding that the CT number of fat is about −130 to −100.

However, because the fat composition ratio in human bodies varies depending on the tissue, the conventional method described above comprising determining a threshold value has problems in that fat cannot be separated solely from other components in tissues and in that the fat composition ratio in ROI (region of interest) cannot be determined.

DISCLOSURE OF INVENTION

Thus, the object of the present invention resides in providing a method for generating a fat distribution image by a CT system, wherein an image representing fat distribution is generated, based on the fat composition ratio in a tissue.

In a first aspect of the present invention, the method for generating a fat distribution image by a CT system wherein an image of fat distribution is generated from a cross sectional image data via X ray comprises the steps of a scanning step wherein scanning is effected at least at two different levels of X-ray tube voltage using a phantom containing a sample rod of a fat standard material in addition to plural sample rods with different densities of a bone mineral equivalent material to generate at least two cross sectional image data, a CT number detecting step wherein the CT number of each pixel in the whole region or an objective region of the cross sectional image data is detected as the "CT number of a tissue including fat", ie. αwf, a linear regression calculating step wherein the CT number of the bone mineral equivalent material is detected in the cross sectional image data following the principle of quantitative measurement of bone mineral mass to calculate a linear regression between the CT number and the density of the bone mineral equivalent material and to define the CT number as the "CT number of a tissue excluding fat", ie. αnf, a fat standard material CT number detecting step wherein the "CT number of the fat standard material", ie. αff is detected in the cross sectional image data, a soft tissue standard material CT number detecting step wherein the CT number of blood in the cross sectional image data is detected as the "CT number of a soft tissue standard material", ie. αst, a CT number application step wherein "α" in the equation α=αwf−αnf is defined as the variation of the CT number due to fat while "β" in the equation α=β·{αff−αst} is defined as a fat ratio parameter and the "CT number of a tissue including fat" ie. αwf, etc., should be applied to the equation $$\alpha wf = \alpha nf + \beta \cdot \{\alpha ff - \alpha st\}$$ Equation (A), a fat ratio parameter calculating step wherein the density of the bone mineral equivalent material and the "CT number of a tissue excluding fat", ie. αnf should be deleted in at least two linear regressions calculated at the linear regression calculating step and in at least two equations (A) to be applied at the CT number application step, to calculate the fat ratio parameter β on the basis of the detected CT number of each pixel at the CT number detecting step, and a fat ratio parameter image generation step wherein an image is generated on the basis of the calculated fat ratio parameter β.

According to the method for generating a fat distribution image by a CT system of the present invention, scanning is effected at least at two different levels of X-ray tube voltage at the scanning step, using a phantom containing a sample rod of a fat standard material in addition to plural sample rods with different densities of a bone mineral equivalent material to generate at least two cross sectional image data.

At the CT number detecting step, the CT number of each pixel in the whole region or an objective region of the cross sectional image data is detected as the "CT number of a tissue including fat", ie. αwf.

At the linear regression calculating step, the CT number of the bone mineral equivalent material is detected in the cross sectional image data following the principle of quantitative measurement of bone mineral mass to calculate a linear regression between the CT number and the density of the bone mineral equivalent material. Then, the CT number is designated the "CT number of a tissue excluding fat", ie. αnf. Furthermore, at least two linear regressions should be calculated, depending on the scanning number at different levels of tube voltage.

At the fat standard material CT number detecting step, the "CT number of the fat standard material", ie. αff is detected in the cross sectional image data, and at the soft tissue standard material CT number detecting step, the CT number of blood in the cross sectional image data is detected as the "CT number of a soft tissue standard material", ie. αst.

At the CT number application step, "β" in the equation α=β·{αff−αst} is defined as a fat ratio parameter while "a" in the equation α=αwf−αnf is defined as the variation of the CT number due to fat, and the "CT number of a tissue including fat" ie. αwf, etc. should be applied to the equation $$\alpha wf = \alpha nf + \beta \cdot \{\alpha ff - \alpha st\}$$ Equation (A).

The above equation (A) is known, so no detailed explanation thereof will now be described.

At the fat ratio parameter calculating step with attention focused on the finding that the density of the bone mineral equivalent material should be constant at scanning at any different level of X-ray tube voltage, the density of the bone mineral equivalent material and the "CT number of a tissue excluding fat", ie. αnf should be deleted in at least two linear regressions calculated at the linear regression calculating step and in at least two equations (A) to be applied from the CT number application step, to calculate the fat ratio parameter β on the basis of the detected CT number of each pixel at the CT number detecting step.

At the fat ratio parameter image generation step, an image is generated on the basis of the calculated fat ratio parameter β. Because the fat ratio parameter "β" is a parameter representing the fat composition ratio in tissues, the generated image displays the distribution of fat (composition ratio).

In a second aspect of the present invention, the method for generating a fat distribution image by a CT system comprises a soft tissue standard material CT number detecting step wherein use is made of a phantom containing a sample rod of a fat standard material and a sample rod of a water equivalent material in addition to plural sample rods with various densities of a bone mineral equivalent material to detect the CT number of the water equivalent material in the cross sectional image data generated from scanning as the "CT number of a soft tissue standard material", ie. αst instead of the soft tissue standard material CT number detecting step wherein the CT number of blood in the cross sectional image data is detected as the "CT number of a soft tissue standard material", ie. αst.

BEST MODE FOR CARRYING OUT THE INVENTION

The present invention will now be explained hereinbelow in examples as shown in figures. But the present invention is not limited to the examples.

Figure 5:
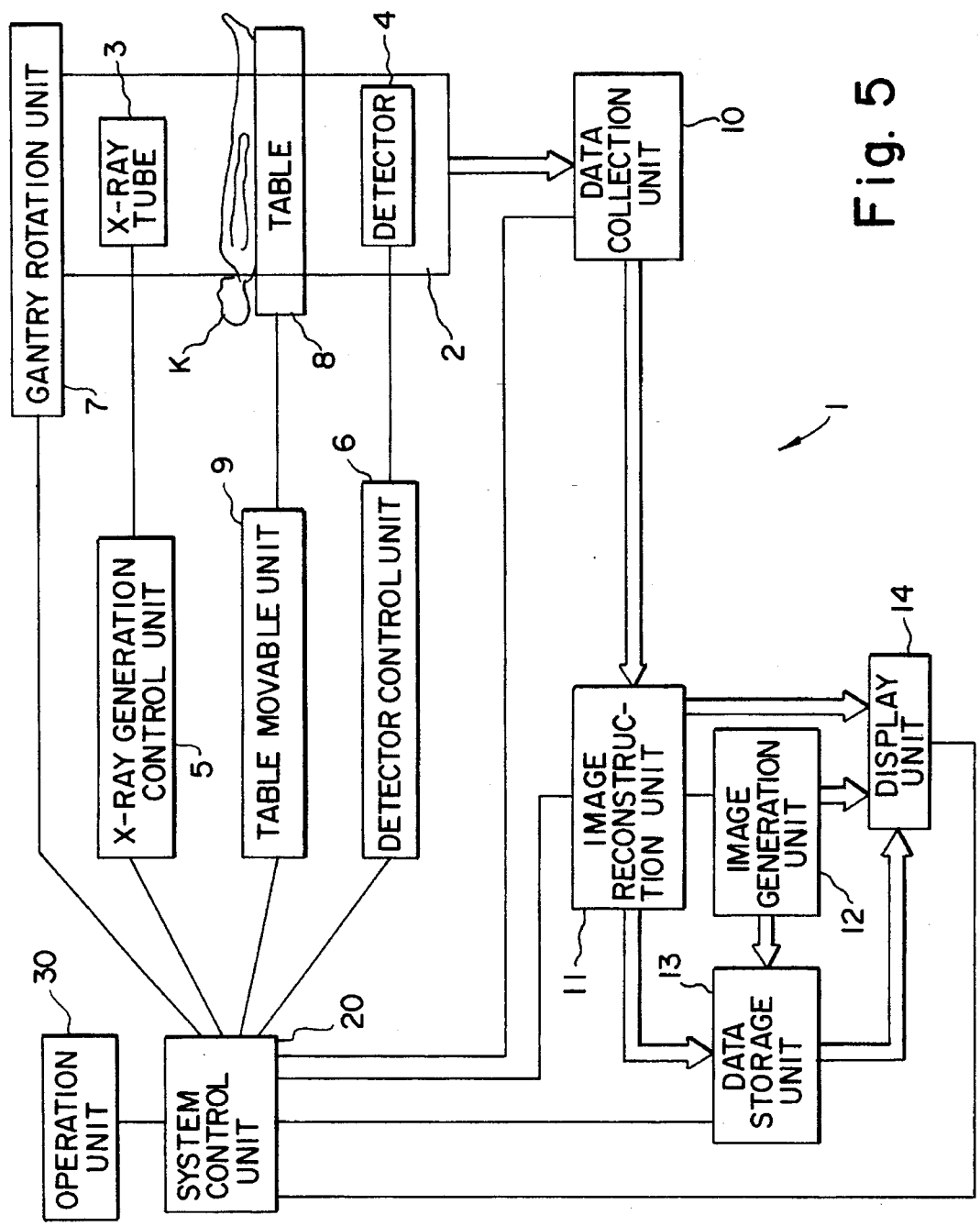
FIG. 5 is a block diagram of a CT system for carrying out the method for generating a fat distribution image in accordance with the present invention.

FIG. 5 is a block diagram of CT system 1 for carrying out the method for generating a fat distribution image in accordance with the present invention.

X-ray tube 3 and detector 4, both placed in gantry 2, are integrally rotated with gantry rotation system 7.

The detector 4 detects the intensity of X-ray transmitted through subject K.

X-ray generation control circuit 5 is connected to x-ray tube 3, to control X-ray generation and the cessation thereof.

Detector control circuit 6 controls the timing to operate detector 4.

Table 8 is for placing the subject K, and is linearly movable with table movable unit 9.

Data collection unit 10 collects projection data from the detector 4.

Image reconstitution unit 11 reconstitutes an image based on the projection data from the data collection unit 10, to output cross sectional image data.

On the basis of the cross sectional image data obtained by the image reconstitution unit 11, image generation unit 12 is for carrying out the procedures of the present invention as described hereinafter, to output new cross sectional image data.

Data storage unit 13 stores the cross sectional image data.

Display unit 14 displays a cross sectional image on the basis of the cross sectional image data from the image reconstitution unit 11 and the image generation unit 12.

System control unit 20 transfers and receives necessary signals to and from X-ray generation control circuit 5, detector control circuit 6, gantry rotation unit 7, table movable unit 9, data collection unit 10, image reconstitution unit 11, image generation unit 12, data storage unit 13, and display unit 14.

Operation unit 30 is for an operator to input commands and the like.

Figure 2:
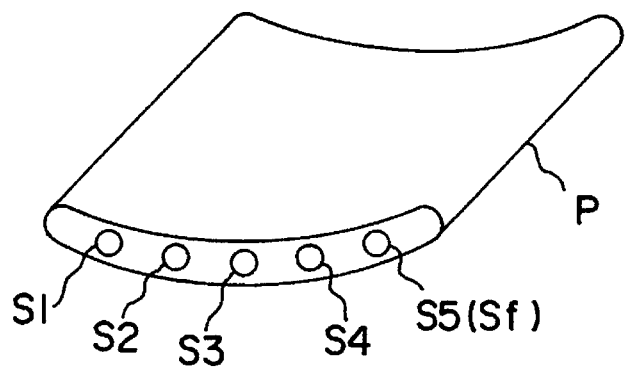
FIG. 2 is an illustration of a phantom to be used in the present invention.

FIG. 2 is an illustrative figure of a phantom to be used for the method for generating a fat distribution image in one example in accordance with the present invention.

The phantom P is a phantom to be used for quantitative BMD (bone mineral density) measurement and is capable of containing plural sample rods S1, S2, . . . with various densities of a bone mineral equivalent material. The bone mineral equivalent material is, for example, potassium hydrogen phosphate, calcium carbonate and the like.

In this example, the phantom P also contains sample rod Sf of a fat standard material, in addition to the sample rods S1, . . . , S4 with various densities of the bone mineral equivalent material.

Figure 1:
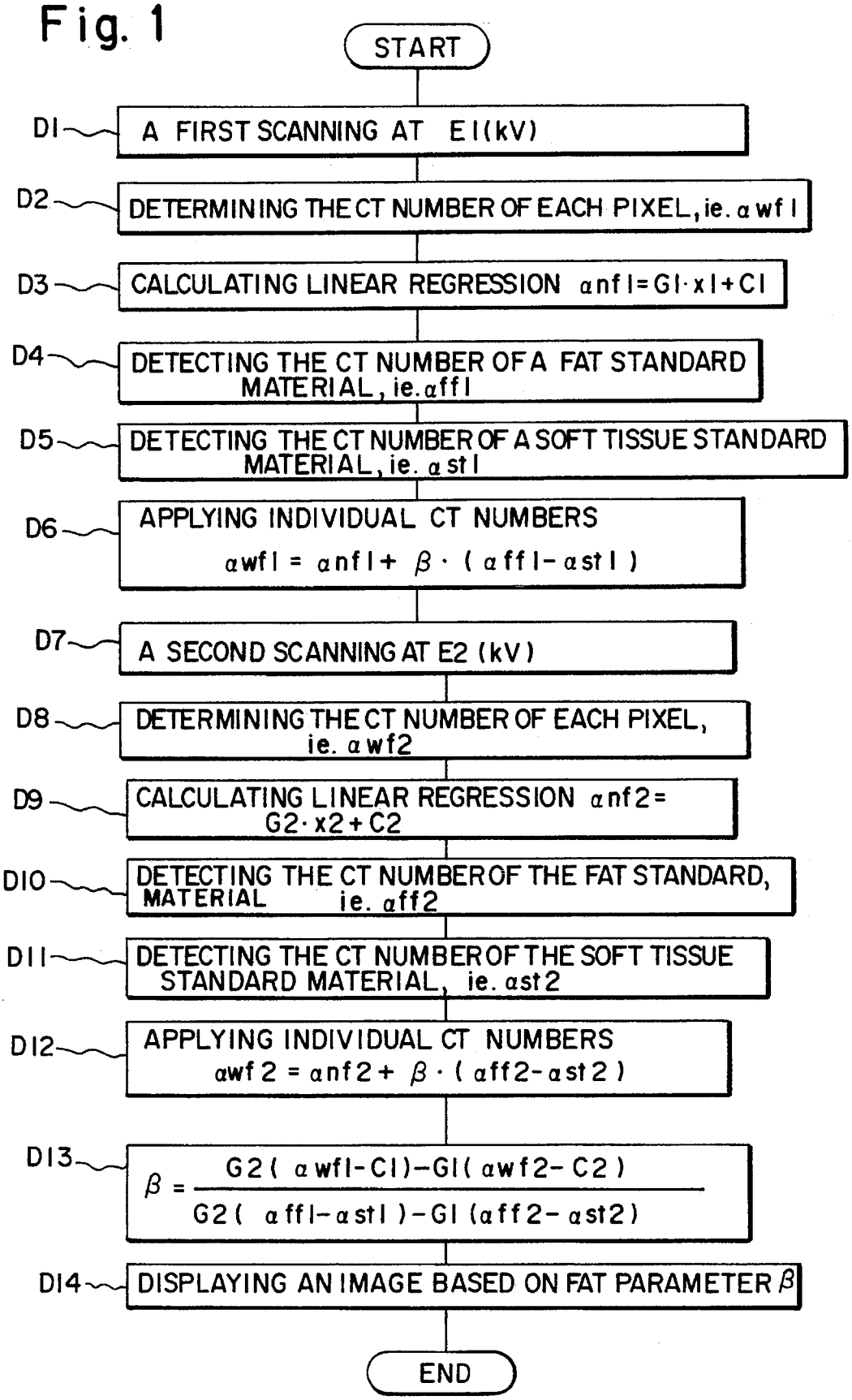
FIG. 1 is a flow chart depicting the procedures of the method of generating a fat distribution image in accordance with the present invention.

FIG. 1 is a flow chart representing the method for generating a fat distribution image in one example in accordance with the present invention. Following the flow chart of FIG. 1, explanation will now be made.

Following the principle of quantitative BMD measurement, phantom P is placed below the waist of subject K. Then, after the third lumbar vertebrae is determined as a scanning cross section, for example, the following procedures will be carried out when an operator directs to commence the generation of a fat distribution image through operation unit 30.

At step D1, a first scanning of the subject K and the phantom P is effected at a X-ray tube voltage of E1 (kV).

At step D2, the CT number of each pixel in the cross sectional image data from the first scanning is designated the CT number of a tissue including fat, ie. αwfl (wf=with fat). The αwfl should be expressed as αwfli when the pixel number is "i", but the "i" is neglected so as to simplify the explanation.

Figure 3:
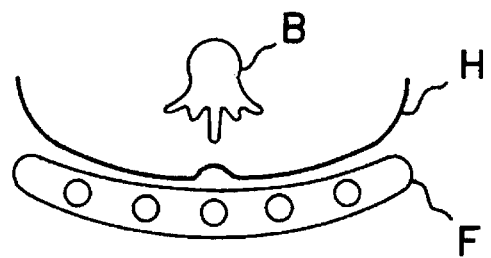
FIG. 3 is an illustration of a cross sectional image in accordance with the present invention.

FIG. 3 shows a schematic view of the cross sectional image from the cross sectional image data. "H" represents contour; and "B" represents third lumbar vertebrae.

Figure 4:
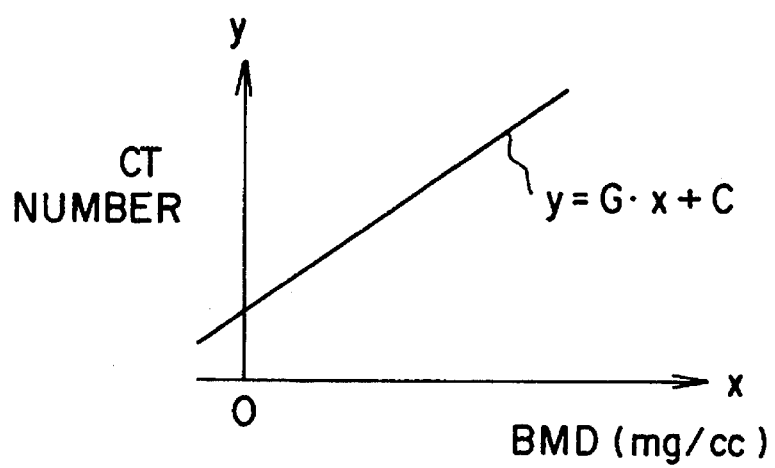
FIG. 4 is an illustration of a linear regression in accordance with the present invention.

At step D3, the CT numbers of the sample rods, S1, . . . , S4 with various densities of the bone mineral equivalent material in the cross sectional image data are detected, to calculate a linear regression by least squares method, as shown in FIG. 4 and represented by the following equation;

$$y = G \cdot x + C \tag{b}$$

wherein X axis represents BMD and y axis represents CT number.

Because the sample rods S1, . . . , S4 with various densities of the bone mineral equivalent material do not contain fat, the CT number on y axis is defined as the "CT number of a tissue excluding fat", ie. αnf (nf=no fat), and the linear regression from the first scanning is now represented as follows;

$$\alpha nfl = G1 \cdot x1 + C1 \tag{b1}$$

At step D4, the CT number of sample rod Sf of a fat standard material, ie. αff1 (ff=full fat) is detected in the cross sectional image data.

At step D5, the CT number of aorta in the cross sectional image data is detected and defined as the CT number of a soft tissue standard material. ie. αst1 (st=soft tissue).

Any tissue on the cross sectional image (data) includes fat. When the CT number of a tissue as ROI is detected and represented as αwf (wf=with fat), the following equation is known;

$$\alpha wf = \alpha nf + \beta \cdot \{\alpha ff - \alpha st\} \quad (A)$$

wherein β is a fat ratio parameter representing the fat composition ratio in a tissue.

At step D6, each CT number detected at the first scanning is applied to the following equation as in the above equation (A);

$$\alpha wf1 = \alpha nf1 + \beta \cdot \{\alpha ff1 - \alpha st1\} \quad (A1)$$

At step D7, then, a second scanning is effected on the subject K and the phantom P at a X-ray tube voltage of E2(kV).

At step D8, the CT number of each pixel in the cross sectional image data from the second scanning is designated the CT number of a tissue including fat, ie. αwf2. The αwf2 should be expressed as αwf2$i$ when the pixel number is "i" but the "i" is neglected so as to simplify the explanation.

At step D9, the CT numbers of the sample rods, S1, ... , S4 with various densities of the bone mineral equivalent material are detected in the cross sectional image data to calculate a linear regression by least squares method, as shown in FIG. 4. Following the same manner as in the above step D3, the linear regression from the second scanning is represented by the following equation;

$$\alpha nf2 = G2 \cdot x2 + C2 \quad (b2)$$

At step D10, the CT number of the sample rod Sf of the fat standard material, ie. αff2 is detected in the cross sectional image data.

At step D11, the CT number of aorta is detected in the cross sectional image data and defined as the CT number of a soft tissue standard material. ie. αst2.

At step D12, each CT number detected from the second scanning is applied to the following equation as in the above equation (A);

$$\alpha wf2 = \alpha nf2 + \beta \cdot \{\alpha ff2 - \alpha st2\} \quad (A2)$$

At step D13, because BMD is constant at scanning at any different X-ray tube voltage so "x" is deleted in the equations (b1) and (b2) provided that x1=x2=x, the fat ratio parameter β is calculated on the basis of the equations (A1) and (A2) by the following equation;

$$\beta = [G2\{\alpha wf1 - C1\} - G1\{\alpha wf2 - C2\}] / [G2\{\alpha ff1 - \alpha st1\} - G1\{\alpha ff2 - \alpha st2\}].$$

As has been described above, because the pixel number "i" is neglected in the expression αwf1 and αwf2 for simplifying explanation (in other words, in the above equations, β should be expressed as β$i$; and αwf1 and αwf2 should be expressed as αwf1$i$ and αwf2$i$, respectively), the step 13 is carried out on any pixel number "i" corresponding to the fat distribution image to be displayed.

At step D14, based on the calculated fat ratio parameter β of each pixel, display unit 14 displays an image of an intensity and a gradation corresponding to the dimension of the fat ratio parameter β.

Because the fat ratio parameter β is a parameter representing the fat composition ratio in a tissue, the image described above represents the distribution of fat (composition ratio).

In the above example, the CT number of aorta in the cross sectional image data is adopted as the CT number of a soft tissue standard material, ie. αst, but use may be made of the CT number of a water equivalent material in the form of a sample rod placed in the phantom p in place of the CT number of aorta.

According to the method for generating a fat distribution image by a CT system, an image representing fat distribution can be generated, based on the fat composition ratio in a tissue.

What is claimed is:

1. A method for generating a fat distribution image by a CT system wherein an image of fat distribution is generated from a cross sectional image data via X ray, comprising the steps of a scanning step wherein scanning is effected at least at two different levels of X-ray tube voltage using a phantom containing a sample rod of a fat standard material in addition to plural sample rods with different densities of a bone mineral equivalent material to generate at least two cross sectional image data, a CT number detecting step wherein the CT number of each pixel in the whole region or an objective region of the cross sectional image data is detected as the "CT number of a tissue including fat", ie. αwf, a linear regression calculating step wherein the CT number of the bone mineral equivalent material is detected in the cross sectional image data following the principle of quantitative measurement of bone mineral mass to calculate a linear regression between the CT number and the density of the bone mineral equivalent material and to define the CT number as the "CT number of a tissue excluding fat", ie. αnf, a fat standard material CT number detecting step wherein the "CT number of the fat standard material", ie. αff is detected in the cross sectional image data, a soft tissue standard material CT number detecting step wherein the CT number of blood in the cross sectional image data is detected as the "CT number of a soft tissue standard material", ie. αst, a CT number application step wherein "α" in the equation α=αwf−αnf is defined as the variation of the CT number due to fat while "β" in the equation α=·{αff−αst} is defined as a fat ratio parameter and the "CT number of a tissue including fat" ie. αwf, etc., is applied to the equation $$\alpha wf = \alpha nf + \beta \cdot \{\alpha ff - \alpha st\} \quad \text{Equation (A)}$$

a fat ratio parameter calculating step wherein the density of the bone mineral equivalent material and the "CT number of a tissue excluding fat", ie. αnf is deleted in at least two linear regressions calculated at the linear regression calculating step and in at least two equations (A) to be applied at the CT number application step, to calculate the fat ratio parameter β on the basis of the detected CT number of each pixel at the CT number detecting step, and a fat ratio parameter image generation step wherein an image is generated on the basis of the calculated fat ratio parameter β.

2. A method for generating a fat distribution image by a CT system wherein an image of fat distribution is generated from a cross sectional image data via X ray, comprising the steps of a scanning step wherein scanning is effected at least at two different levels of X-ray tube voltage using a phantom containing a sample rod of a fat standard material and a sample rod of a water equivalent material in addition to plural sample rods with different densities of a bone mineral equivalent material to generate at least two cross sectional image data, a CT number detecting step wherein the CT number of each pixel in the whole region or an objective region of the cross sectional image data is detected as the "CT number of a tissue including fat", ie. αwf, a linear regression calculating step wherein the CT number of the bone mineral equivalent material is detected in the cross sectional image data following the principle of quantitative measurement of bone mineral mass to calculate a linear regression between the CT number and the density of the bone mineral equivalent material and to define the CT number as the "CT number of a tissue excluding fat", ie. $\alpha nf$, a fat standard material CT number detecting step wherein the "CT number of the fat standard material", ie. $\alpha ff$ is detected in the cross sectional image data, a soft tissue standard material CT number detecting step wherein the CT number of the water equivalent material in the cross sectional image data is detected as the "CT number of a soft tissue standard material", ie. $\alpha st$, a CT number application step wherein "$\alpha$" in the equation $\alpha = \alpha wf - \alpha nf$ is defined as the variation of the CT number due to fat while "$\beta$" in the equation $\alpha = \beta \cdot \{\alpha ff - \alpha st\}$ is defined as a fat ratio parameter and the "CT number of a tissue including fat" ie. $\alpha wf$, etc., is applied to the equation $$\alpha wf = \alpha nf + \beta \cdot \{\alpha ff - \alpha st\} \qquad \text{Equation (A)}$$

a fat ratio parameter calculating step wherein the density of the bone mineral equivalent material and the "CT number of a tissue excluding fat", ie. $\alpha nf$ is deleted in at least two linear regressions calculated at the linear regression calculating step and in at least two equations (A) to be applied at the CT number application step, to calculate the fat ratio parameter $\beta$ on the basis of the detected CT number of each pixel at the CT number detecting step, and a fat ratio parameter image generation step wherein an image is generated on the basis of the calculated fat ratio parameter $\beta$.

* * * * *